(12) United States Patent
Übelacker et al.

(10) Patent No.: US 12,351,089 B2
(45) Date of Patent: Jul. 8, 2025

(54) VEHICLE SEAT AND METHOD FOR OPERATING A VEHICLE SEAT

(71) Applicant: GRAMMER AG, Ursensollen (DE)

(72) Inventors: Roland Übelacker, Pfreimd (DE); Konstantin Krivenkov, Amberg (DE)

(73) Assignee: GRAMMER AG, Ursensollen (DE)

( * ) Notice: Subject to any disclaimer, the term of this patent is extended or adjusted under 35 U.S.C. 154(b) by 930 days.

(21) Appl. No.: 17/271,777

(22) PCT Filed: Aug. 27, 2019

(86) PCT No.: PCT/EP2019/072748
§ 371 (c)(1),
(2) Date: Feb. 26, 2021

(87) PCT Pub. No.: WO2020/043679
PCT Pub. Date: Mar. 5, 2020

(65) Prior Publication Data
US 2021/0323453 A1 Oct. 21, 2021

(30) Foreign Application Priority Data

Aug. 28, 2018 (DE) .......................... 102018120996.7
Aug. 20, 2019 (DE) .......................... 102019122278.8

(51) Int. Cl.
*B60N 2/56* (2006.01)
*A61L 2/00* (2006.01)

(52) U.S. Cl.
CPC .......... *B60N 2/565* (2013.01); *B60N 2/5642* (2013.01); *B60N 2/5678* (2013.01); *A61L 2/0023* (2013.01); *A61L 2202/25* (2013.01)

(58) Field of Classification Search
CPC ..... A61L 2/0023; A61L 2202/25; B60N 2/56; B60N 2/5607; B60N 2/5621;
(Continued)

(56) References Cited

U.S. PATENT DOCUMENTS 5,934,748 A 8/1999 Faust et al.
6,291,803 B1 9/2001 Fourrey
(Continued)

FOREIGN PATENT DOCUMENTS

CN 1535220 10/2004
CN 103587446 2/2014
(Continued)

OTHER PUBLICATIONS

Official Action with English Translation for China Patent Application No. 201980055712.4, dated Jun. 22, 2022, 13 pages.
(Continued)

*Primary Examiner* — Sang Y Paik
*Assistant Examiner* — Bonita Khlok
(74) *Attorney, Agent, or Firm* — Sheridan Ross P.C.

(57) ABSTRACT

A vehicle seat comprising at least one seat element in which at least one heating device and at least one ventilation device are provided. The vehicle seat comprises a sensor device, which has at least one temperature sensor and at least one moisture sensor. A closed-loop/open-loop control device controls the heating device and/or the ventilation device in an open-loop or closed-loop manner on the basis of the data from the sensor device with respect to the comfort parameters of temperature and/or moisture content, whereby the seat climate can be actively controlled in an open-loop or closed-loop manner.

15 Claims, 13 Drawing Sheets

(58) Field of Classification Search
CPC .... B60N 2/5642; B60N 2/565; B60N 2/5657; B60N 2/5678; B60N 2/90; B60N 2/002
USPC ........................................ 219/202, 497, 518
See application file for complete search history.

(56) References Cited

U.S. PATENT DOCUMENTS

| | | | |
|---|---|---|---|
| 6,892,807 | B2 | 5/2005 | Fristedt et al. |
| 9,511,646 | B2 | 12/2016 | Muller et al. |
| 2006/0244289 | A1* | 11/2006 | Bedro ................. B60N 2/5621 297/180.1 |
| 2015/0239321 | A1* | 8/2015 | Muller ............... B60H 1/00792 297/217.2 |
| 2016/0304013 | A1* | 10/2016 | Wolas ................. B60N 2/5657 |
| 2018/0257523 | A1* | 9/2018 | Dacosta-Mallet ..... B60N 2/565 |
| 2019/0331624 | A1* | 10/2019 | Singuru ............ B60H 1/00285 |
| 2019/0389346 | A1* | 12/2019 | Hayakawa ........... B60N 2/5685 |

FOREIGN PATENT DOCUMENTS

| | | |
|---|---|---|
| CN | 104736387 | 6/2015 |
| DE | 19726810 | 10/1998 |
| DE | 102013003673 | 3/2014 |
| DE | 102016219203 | 4/2018 |

OTHER PUBLICATIONS

Official Action for German Patent Application No. 102019122278. 8, dated Nov. 26, 2020, 7 pages.
International Search Report and Written Opinion for International (PCT) Patent Application No. PCT/EP2019/072748, dated Nov. 22, 2019, 11 pages.
Translation of the International Search Report for International (PCT) Patent Application No. PCT/EP2019/072748, dated Nov. 22, 2019, 2 pages.
Article 19 Amendments with English Translation for International (PCT) Patent Application No. PCT/EP2019/072748, dated Jan. 16, 2020, 12 pages.
Official Action with English Translation for China Patent Application No. 201980055712.4, dated Nov. 21, 2022, 14 pages.
Official Action with Machine Translation for European Patent Application No. 19759363.5, dated Feb. 7, 2023, 9 pages.
Official Action for German Patent Application No. 102019122278. 8, dated Mar. 20, 2023, 9 pages.

* cited by examiner

VEHICLE SEAT AND METHOD FOR OPERATING A VEHICLE SEAT

CROSS REFERENCE TO RELATED APPLICATIONS

This application is a national stage application under 35 U.S.C. 371 and claims the benefit of PCT Application No. PCT/EP2019/072748 having an international filing date of 27 Aug. 2019, which designated the United States, which PCT application claimed the benefit of German Patent Application No. 10 2018 120 996.7 filed 28 Aug. 2018, and German Patent Application No. 10 2019 122 278.8 filed 20 Aug. 2019, the disclosures of which are incor-porated herein by reference in their entirety.

FIELD

The invention relates to a seat for a vehicle and to a method for operating a seat for a vehicle.

BACKGROUND

In conventional vehicle seats, there is often the problem of insufficient air circulation between the seat and the person sitting on the seat. Moisture, in particular sweat, can therefore no longer be sufficiently absorbed by the ambient air in the contact regions of the user with the seat. This can occur in particular on longer journeys, for example in the case of seats in com-mercial vehicles in which the user is known to spend a long time.

The body fluid is then absorbed through the seat or the upholstery. A damp seat can be perceived as uncomfortable by the user. In addition, the moisture environment promotes bacte-rial growth.

Conventional seats often have a seat heater or a ventilation device that is activated by the user. However, upon activation, the user is usually already cool, sweaty, damp or wet, whereby the moisture is absorbed by the seat or the seat cushions. Furthermore, ventilated seats often cool the skin surface too much, which can cause tension or back problems for the user.

SUMMARY

The aim of the invention is accordingly to provide a seat for a vehicle and a method for operating a seat for a vehicle which solve the problems mentioned at the outset.

According to a preferred concept of the invention, the seat comprises at least one sensor device. The sensor device preferably has at least one temperature sensor and/or at least one moisture sensor, which can acquire the comfort parameters of temperature and/or moisture in the seat, in particular on or near the surface of the seat. Furthermore, it is advantageous if the comfort parameters can be acquired under the surface or in the middle of the upholstery structure. When the seat is occupied, this surface is preferably in contact with the user. The sensor device can, however, also comprise further sensors by means of which sensor data of the most varied of types can be detected.

The seat preferably also has a closed-loop/open-loop control device which controls the seat climate in an open-loop or closed-loop manner on the basis of the comfort parameters. The sensor device is therefore preferably connected to the closed-loop/open-loop control device via signals. The seat climate can preferably be actively controlled in an open-loop or closed-loop manner by means of the closed-loop/open-loop control device, the control of the seat climate in an open-loop or closed-loop manner being understood to mean the control of the comfort parameters in an open-loop or closed-loop manner.

Open-loop control is usually understood as meaning that an output variable is produced on the basis of an input signal. An input signal of this type is generally a binary variable, for example In/Out. Closed-loop control is based on feedback from an output signal. During closed-loop control, the controlled variable is continuously compared with a target value. The closed-loop controller determines a manipulated variable, according to the difference of the values, which manipulated variable acts on the controlled variable so that it minimises the difference and the controlled variable assumes a desired time response even if disturbance variables are present.

The closed-loop/open-loop control device preferably controls a heating device and a ventilation device of the seat in an open-loop or closed-loop manner, as a result of which the seat climate can be actively controlled accordingly.

An essential point of the invention is a vehicle seat, comprising at least one seat element in which at least one heating device and at least one ventilation device are provided, the vehicle seat comprising a sensor device which has at least one temperature sensor and at least one moisture sensor, a closed-loop/open-loop control device controlling the heating device and/or the ventilation device in an open-loop or closed-loop manner on the basis of the data from the sensor device with respect to the comfort parameters of temperature and/or moisture content, whereby the seat climate can be actively controlled in an open-loop or closed-loop manner.

With a vehicle seat of this type, the seat climate is adapted according to the comfort parameters before the user feels the unpleasant consequences of a less than optimal seat climate. Unpleasant consequences of this type are, as already mentioned, coolness, sweating, moisture or wetness, which can cause tension or back pain in the user.

Of course, the term comfort parameters can also include further data. For this purpose, further sensors can also be present which are connected to the closed-loop/open-loop control device via signals. Sensors of this type can also be arranged outside the vehicle seat.

For example, sensors that analyse driving behaviour would be conceivable. In the event of abnormal driving behaviour, for example due to fatigue, the closed-loop/open-loop control device could activate specific devices, for example cool the seat.

Furthermore, in addition to the heating device and the ventilation device, the closed-loop/open-loop control device can advantageously be connected to other devices via signals and control them accordingly in an open-loop or closed-loop manner.

It would also be conceivable to control the heating device and/or the ventilation device on the basis of predetermined points in time. This can comprise heating the seat in the morning on a cold winter day, for example.

According to a preferred embodiment, the closed-loop/open-loop control device has a storage device in which target values or target ranges are stored for the comfort parameters or target values or target ranges are stored for comfort parameter combinations. These target values represent predetermined comfort limits of the comfort parameters or the comfort parameter combinations. The closed-loop/open-loop control device advantageously compares the data provided by the sensor device with the corresponding target values or comfort limits. Active control of the comfort parameters or the seat climate is then preferably carried out by the automatic control of the heating device and/or the ventilation device by the closed-loop/open-loop control device. The closed-loop/open-loop control device advantageously controls individual comfort parameters in an open-loop or closed-loop manner. For example, a specific temperature value or moisture content can be set accordingly. However, for optimal seat air conditioning it is often necessary to predetermine specific comfort parameter combinations. Accordingly, with a specific moisture content, a specific predeterminable temperature range or a specific predetermined temperature would be optimal. Comfort parameter combinations of this type can be stored as target values or target ranges in the storage device.

According to a further preferred embodiment, an input device is connected to the closed-loop/open-loop control device via signals. The user can advantageously set the comfort parameters, for example the temperature or the moisture content, directly by means of the input device. It is also advantageous that the target values or the target ranges of the comfort parameters or the comfort parameter combinations can be manipulated by means of the input device and/or can be entered in the storage device by means of the input device.

According to a preferred embodiment, the seat comprises two seat elements. A seat element is advantageously a lower seat part, i.e. that part of the seat on which the user sits. The further seat element is advantageously a backrest element. It is advantageous that the sensor device comprises at least one temperature sensor and at least one moisture sensor for the lower seat part and at least one temperature sensor and at least one moisture sensor for the backrest element. Accordingly, the seat climate can be actively controlled both in the lower seat part and in the backrest element. Corresponding closed-loop control can take place in both seat elements at the same time. Alternatively, an active control in an open-loop or closed-loop manner in the individual seat elements can take place independently of one another. Advantageously, it can be selected by the input device for which seat element an active seat air conditioning should take place, if not for both seat elements.

The seat elements, the lower seat part and the backrest element, each advantageously comprise a height direction Z, Z'. The height direction Z, Z' is to be understood such that the uppermost layer of the seat element is that which is in contact with the user and the lowest element is the one which is furthest away from the user.

According to a preferred embodiment, the at least one seat element comprises a first layer which is made of a material that can absorb and conduct moisture. The material of the first layer is advantageously designed so as to be porous and/or open-pored. The first layer preferably consists of a moisture-conducting foam or a moisture-conducting fabric. This material is advantageously open-pored and is suitable for absorbing moisture immediately and then passing it on accordingly. It would also be conceivable that the material of the first layer is a fleece, a woven fabric, a knitted fabric or a knitted spacer fabric.

The surface of the first layer is advantageously in direct contact with the user or in close proximity to the user when the seat is occupied. It would also be conceivable to arrange further layers over the first layer; these layers should also be moisture-conducting. It can be advantageous, for example, that this first layer is covered by a likewise moisture-conducting cover, for example a moisture-conducting fabric cover. Accordingly, the contact with the user can be direct or indirect through the cover in between.

According to a further preferred embodiment, the at least one temperature sensor and/or the at least one moisture sensor are arranged in the at least one seat element such that the comfort parameters of temperature and/or moisture can be acquired on or near the surface of the seat element. Furthermore, it is advantageous that the comfort parameters of temperature and/or moisture can be acquired under the surface or in the upholstery structure. It can also be advantageous to acquire the comfort parameters in a specific layer, for example the first layer. Furthermore, a heating device and a ventilation device are advantageously arranged in the at least one seat element, as a result of which the comfort parameters or the seat climate can be actively controlled.

According to a further preferred embodiment, at least one temperature sensor and/or at least one moisture sensor are arranged in both seat elements, i.e. both in the lower seat part and in the backrest element, as a result of which the comfort parameters of temperature and/or moisture can be acquired on or near the surfaces of the seat elements. Furthermore, at least one heating device and at least one ventilation device are advantageously arranged in the two seat elements, as a result of which the comfort parameters or the seat climate can be controlled in an open-loop or closed-loop manner.

According to a further preferred embodiment, the at least one temperature sensor and/or the at least one moisture sensor is/are arranged in and/or above and/or under the first layer. The term "under" the first layer can mean on the one hand that the sensors are located directly under the first layer. However, it can also be possible for further layers to be located between the first layer and the sensors. The term "above the first layer" can be interpreted analogously. It would also be conceivable that the at least one temperature sensor and/or the at least one moisture sensor is/are arranged in the cover which is arranged on the first layer.

It is advantageous that the closed-loop/open-loop control device are evaluated the data transmitted by the sensor device depending on the distance between each sensor and the surface of the at least one seat element in contact with the user. Due to the advantageous consideration of the distance to the user, the seat climate can be set in a significantly more precise manner. Furthermore, it would be conceivable that material characteristics of the ma-terials between the user and the sensor are taken into consideration. Material parameters of this type can comprise, for example, absorption, capacities of the layers with respect to moisture.

According to a preferred embodiment, the heating device and the ventilation device are arranged in the at least one seat element. At least one heating device is advantageously arranged under the first layer in the height direction Z, Z' of the seat element. The term "under" the first layer can mean on the one hand that the heating device is located directly under the first layer. However, it can also be possible for further layers to be located between the first layer and the heating device. It would be conceivable that exactly one heating device is arranged under the first layer in the height direction of the seat element. It would also be conceivable that two or more heating devices are arranged under the first layer.

Analogously, the at least one ventilation device is arranged under the first layer in the height direction Z, Z' of the seat element.

It would also be conceivable that at least one heating device is arranged above the first layer. Furthermore, it would be possible to arrange at least one heating device above and at least one heating device under the first layer.

According to a further preferred embodiment, an intermediate space is arranged under the first layer, which is filled with a preferably gaseous fluid, for example air. A heating device is preferably provided under and/or above this intermediate space. The air located in the intermediate space is advantageously heated by the heating device and can thus absorb more moisture.

According to a further preferred embodiment, the at least one seat element comprises at least one further first layer which is arranged under the first layer. This at least one further first layer also consists of a material that can absorb and conduct moisture. An intermediate space is advantageously provided between and/or under the first layers, which intermediate space is filled with a preferably gaseous fluid, for example air. A heating device is preferably provided under and/or above these intermediate spaces. The air located in the intermediate spaces is advantageously heated by the particular heating device and can thus absorb more moisture.

The at least one heating device is advantageously arranged over the surface, preferably over the entire surface, under the first layer. This allows the first layer to be effectively heated.

According to a further embodiment, a spacer fabric is arranged under the first layer in the height direction Z, Z' of the at least one seat element. The term "under" the first layer can mean on the one hand that the spacer fabric is located directly under the first layer. However, it can also be possible for further layers to be located between the first layer and the spacer fabric. Such a spacer fabric has high air permeability and good cushioning properties.

At least one heating device is preferably arranged between the first layer and the spacer fabric. Accordingly, a spacer fabric is arranged under at least one heating device in the height direction Z, Z' of the seat element.

A shaped element is advantageously arranged at least in portions under the spacer fabric in the height direction Z, Z' of the at least one seat element. The shaped element consists of a material that provides a corresponding resistance or padding with respect to the pressure load caused by contact with the user. Furthermore, the shape of the shaped element substantially defines the shape of the seat element. The shaped element can preferably consist of a cold foam. However, it would also be conceivable for the shaped element to consist of another suitable shaping material. The shaped element preferably has a fan region in which a plurality of ventilation ducts are provided. Furthermore, it is advantageous that the shaped element has a region bordering the fan region. This bordering region can have side bolsters. In a preferred embodiment, a corresponding control of the seat climate in an open-loop or closed-loop manner is not provided in this region, since the user generally only has little contact with such side bolsters.

The ventilation ducts of the fan region are preferably connected to the at least one ventilation device. If two seat elements are provided in the form of a lower seat part and a backrest element, an active control of the seat climate of only the lower seat part or only the backrest element can be provided in an open-loop or closed-loop manner, as already described. However, active control of the seat climate of both the lower seat part and the backrest element can also be provided in an open-loop or closed-loop manner. For this purpose, the two seat elements can advantageously each be assigned a ventilation device which can also be controlled individually according to the sensor data. However, it would also be conceivable that the ventilation ducts are connected to only one ventilation device. An individual venting of the two seat elements could take place through an advantageous locking device which is arranged in the respective connecting ducts between the ventilation device and the particular seat element. With the aid of this locking device, it can be determined which seat element is being ventilated. Optionally, both seat elements can also be ventilated at the same time.

The seat element can preferably also have further layers which are located under, above or between the components already mentioned. These layers can have different characteristics and also have different properties. It is also possible that the seat structure described can be assembled differently in terms of position and orientation with the components described.

The structure of the seat element described above can apply to the lower seat part as well as to the backrest element.

According to a further preferred embodiment, the at least one seat element can be heated by at least one heating device. Moisture is advantageously absorbed in the first layer of the seat element. Furthermore, air is preferably enclosed in the first layer. When heated, at least some of this moisture changes into the gaseous state, depending on the temperature. In addition, the air in the seat element is heated, which can thus absorb more moisture. Accordingly, the steam pressure advantageously increases in the seat element. Steam is thus generated in the seat element. Steam of this type can ideally be a pure gaseous phase or a mixture of liquid and gaseous components.

The change in the physical state can result in a further advantage in the form of increased cooling of the surface of the seat element due to the evaporation heat to be applied.

The steam generated by heating is advantageously conveyed out of the seat element by means of the ventilation device. Advantageously, the ventilation device works in suction mode. The steam can therefore advantageously be drawn out of the seat element through the ventilation device. Since heating the seat element causes the steam to have a higher temperature than the corresponding surrounding air volume, a differential pressure arises which can cause an increased flow speed of the steam. As a result of this increased air speed due to the thermal current and the suction operation of the ventilation device, the steam or moisture can be quickly removed from the seat element.

However, it would also be conceivable that the ventilation device is in a blowing mode. Air can thus be introduced into the first layer, whereby the steam is forced out of the first layer or removed from the first layer.

According to a preferred embodiment, the sensor device comprises a seat occupancy sensor which detects the comfort parameter of seat occupancy. As a result of the advantageous detection of seat occupancy, specific preferred modes which require that no seat occupancy be present can be carried out automatically. The seat occupancy sensor can be arranged at any suitable position in the at least one seat element.

According to a further preferred embodiment, the control of the seat climate takes place by alternating heating and ventilating of the first layer. Advantageously, the at least one heating device and/or the at least one ventilation device can be switched on and off at predetermined intervals. The at least one heating device is advantageously switchable at intervals such that substantially no temperature change takes place on the surface of the seat element. The term "substantially no temperature change" is to be interpreted in such a way that a temperature change is in a range that is not noticeable to the user. Such a temperature change can therefore preferably be in a range from 0° C. to 10° C., more preferably from 0° C. to 5° C., more preferably from 0° C.

to 2.5° C., more preferably from 0° C. to 1° C. The heating intervals are accordingly designed to be short such that, although the moisture in the seat element or the first layer can be converted accordingly, the heating does not take place long enough for the surface of the seat element that is in contact with the user to warm up noticeably for the user. The moisture converted into steam can thus be effectively removed by the ventilation device without the seat heating up noticeably to the user.

Preferably, the at least one heating device and/or the at least one ventilation device can be switched on and off at predetermined intervals. Advantageously, the at least one heating device is switched on at intervals such that the surface of the seat element is not heated during heating of the seat or the seat element.

Usually the heat propagation is inversely proportional to the propagation length which, in the present case, is at the height of the first layer. An interval length can accordingly be measured such that no substantial temperature change occurs on the surface of the seat element which is perceived by the user. Humans detect heat very late, i.e. the surface temperature can be exceeded for a short time without the user noticing. With a configuration of this type, the seat can preferably be air-conditioned during seat occupancy.

Heat conduction is advantageously determined from the thermal coefficient of the first layer ($\lambda$), the temperature difference (T) between the heating device and the surface of the first layer and the height (h) as follows:

$$\lambda * T * 1/h.$$

It can be advantageous if the ventilation device is operated continuously at the same time. Alternatively, the ventilation device can be operated in an alternating manner with the at least one heating device.

The at least one seat element can accordingly be kept in a comfort range. Such a temperature comfort range is preferably between 28° C. and 38° C., ideally 32±5° C. A moisture comfort range is preferably between 10% and 85%, ideally 50% relative moisture.

The at least one heating device and the at least one ventilation device are preferably operated depending on the continuously detected comfort parameters. By advantageously activating the heating device and/or the ventilation device, the comfort parameters can be trans-ferred to the comfort range. For example, if the detected relative moisture values are above a comfort range, this moisture can effectively be carried away from the first layer and also from the driver's clothing.

According to a further embodiment, the comfort range of the comfort parameters can be set by alternating heating and ventilation of the first layer. The comfort range can thus be reached quickly, in particular when the seat is not occupied. The advantageous heating in turn creates steam or steam pressure in the at least one seat element. This steam can be distributed in the at least one seat element and can be quickly sucked away by advantageously switching on the ventilation device in an alternating manner.

Due to the lack of seat occupancy, the first layer can be heated to a higher temperature, as a result of which more liquid is correspondingly converted into the gas phase, or the air in the vehicle seat can absorb even more liquid. The at least one seat element can thus quickly be brought back into the comfort range during an occupancy break.

For this purpose, the vehicle seat advantageously has seat occupancy detection. Alternatively, a manual setting apparatus can also be provided, by means of which the various modes can be selected.

By advantageously alternating heating and ventilation of the first layer, self-cleaning or disinfection of this first layer can take place. The advantageous removal of moisture from the first layer removes the breeding ground for bacteria. The dehumidification is advantageously carried out by targeted heating and venting of the first layer.

According to a further concept of the invention, antibacterial cleaning or disinfection of the seat element takes place by increasing the seat temperature to a temperature at which bacteria and germs cannot survive. The temperature is preferably increased to above 80° C. As a result, bacteria and germs located in the at least one seat element can be effectively killed. This advantageously takes place when the seat is not occupied. For this purpose, it is not necessary to detect the comfort parameters "temperature" and "moisture" by means of the comfort parameter sensors.

A preconditioning of the seat element can preferably take place. This means setting the comfort parameters prior to seat occupancy. The preconditioning preferably starts after a predeterminable start event. Such a start event can be, for example, reaching a time limit. Accordingly, the closed-loop/open-loop control device would comprise a time element, a clock or the like or would be connected to such an element via signals. The closed-loop/open-loop control device then controls the comfort parameters of the seat element in the comfort range in an open-loop or closed-loop manner. Such a start event can for example be the unlocking of the vehicle, or an approach of the user to the vehicle, which is detected by a corresponding sensor.

In the embodiments described above, one seat element or a plurality of seat elements, for example a lower seat part and a backrest element, can be operated accordingly.

The object is also achieved by a method for operating a vehicle seat.

Such a method for operating a vehicle seat, which has at least one seat element in which a heating device and a ventilation device are provided, comprises the following method steps:

a) acquiring sensor data by the sensor device which has at least one temperature sensor and at least one moisture sensor;

b) optionally comparing the acquired sensor data with predetermined target values by the closed-loop/open-loop control device;

c) activating at least one heating device and/or at least one ventilation device by the closed-loop/open-loop control device.

The method can be equipped with all the features already described above in the scope of the apparatus individually or in combination with each other and vice versa.

The apparatus is preferably suitable and intended to carry out the described embodiments of the method (in particular individual ones and/or a plurality thereof).

Different operating modes can advantageously be set in the method. This can advantageously be done using a suitable input device. The methods advantageously differ in whether the seat is occupied or not. Accordingly, step a) advantageously also comprises acquiring sensor data from a seat occupancy sensor.

According to a preferred embodiment, when the seat is not occupied, an antibacterial cleaning of the seat element is carried out by the closed-loop/open-loop control device (9) in which the at least one heating device (10) is activated so that the at least one seat element is brought to a temperature at which bacteria and germs are killed, this temperature being 80° C.

The ventilation device is preferably operated at the same time during the antibacterial cleaning. Alternatively, the heating device and the ventilation device can be operated in an alternating manner. The advantageous removal of moisture from the at least one seat element, or from the first layer of the at least one seat element, removes the breeding ground for bacteria. The dehumidification is advantageously carried out by targeted heating and venting of the first layer. By advantageously alternating heating and ventilation of the first layer, self-cleaning or disinfection of this first layer can take place.

According to a preferred embodiment, when the seat is occupied, the at least one heating device and the at least one ventilation device are activated at alternating intervals by the closed-loop/open-loop control device. The length of the interval for an activation of the at least one heating device is advantageously designed such that there is substantially no temperature change on the surface of the seat element. The term "substantially no temperature change" is to be interpreted in such a way that a temperature change is in a range that is not noticeable to the user. Such a temperature change can therefore preferably be in a range from 0° C. to 10° C., more preferably from 0° C. to 5° C., more preferably from 0° C. to 2.5° C., more preferably from 0° C. to 1° C. However, the amount of heat introduced into the first layer is sufficient to convert a sufficient amount of moisture into steam. The steam generated can preferably consist of a gas phase and optionally a liquid phase.

The advantageous method of activating the heating device and the ventilation device at alternating intervals can be used advantageously when the moisture value is above the comfort limit. At the same time, however, the temperature value is within or above the comfort limits. This mode can be used to remove moisture from both the seat element and the user's clothing, causing them to dry.

If the temperature is below the comfort range, the interval length can be adapted accordingly so that a sufficient amount of heat is introduced into the seat element or the first layer of the seat element so that the temperature thereof is brought back into the comfort range.

Such a temperature comfort range is preferably between 28° C. and 38° C., ideally 32±5° C. A moisture comfort range is preferably between 10% and 85%, ideally 50% relative moisture.

According to a preferred embodiment, when the seat is not occupied, the at least one heating device and the at least one ventilation device are activated at alternating intervals by the closed-loop/open-loop control device. The interval length for activation of the at least one heating device is advantageously designed such that the at least one seat element is heated to a temperature which is above a predetermined comfort range. The temperature comfort range is preferably between 28° C. and 38° C. More preferably, the temperature comfort range is 32±5° C. Accordingly, in this mode there is a temperature change on the surface of the seat element, which is, however, insignificant due to the non-occupancy of the seat. By using a higher temperature, more liquid will correspondingly change into the gas phase, or the air in the vehicle seat will be able to absorb even more liquid. The at least one seat element can thus be brought back into the comfort range more quickly during an occupancy break.

According to a further preferred embodiment, when a predetermined start event occurs, a preconditioning of at least one seat element takes place, during which preconditioning the comfort parameters are brought into the predetermined comfort range by the closed-loop/open-loop control device by activating the at least one heating device and/or the at least one ventilation device. This means setting the comfort parameters prior to seat occupancy. The preconditioning preferably starts after a predeterminable start event. Such a start event can be, for example, reaching a time limit. Accordingly, the closed-loop/open-loop control device would comprise a time element, a clock or the like or would be connected to such an element via signals. The closed-loop/open-loop control device then controls the comfort parameters of the seat element in the comfort range in an open-loop or closed-loop manner. Such a start event can for example be the unlocking of the vehicle, or an approach of the user to the vehicle, which is detected by a corresponding sensor.

Further advantages, aims and properties of the present invention will be explained with reference to the following description of the accompanying drawings. Similar components may have the same reference signs in the various embodiments.

DETAILED DESCRIPTION

Figure 1A:
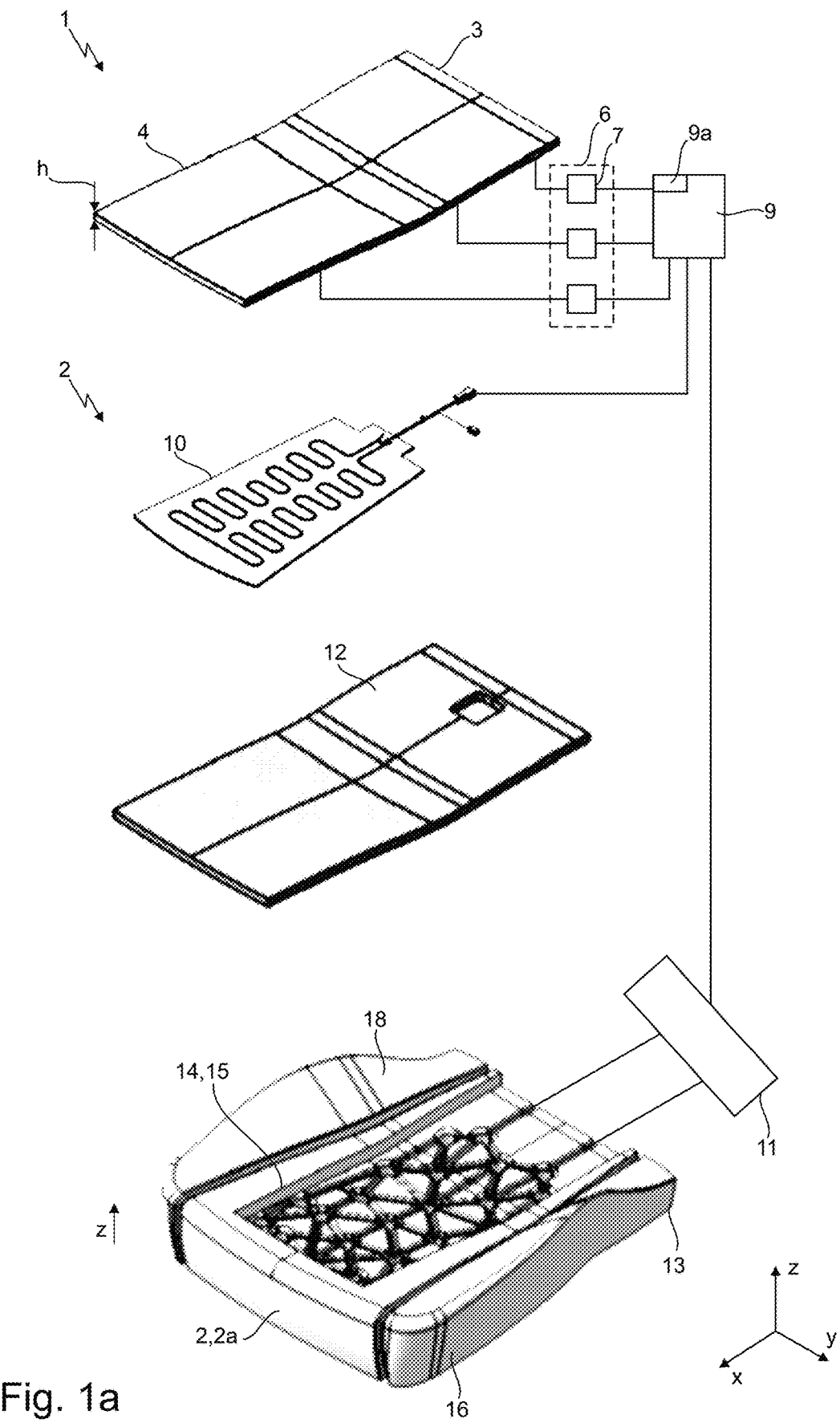
FIG. 1a shows a seat element according to one embodiment of the invention.

In FIGS. 1a, 1b, 1c and 2, the structure of a seat (1) or a seat element (2) is shown. Such a vehicle seat (1) comprises at least one seat element in which at least one heating device (10) and at least one ventilation device (11) are provided, the vehicle seat (1) comprising a sensor device (6) which has at least one temperature sensor (7) and at least one moisture sensor (8), a closed-loop/open-loop control device (9) controlling the heating device (10) and/or the ventilation device (11) in an open-loop or closed-loop manner on the basis of the data from the sensor device (6) with respect to the comfort parameters of temperature and/or moisture content, whereby the seat climate can be actively controlled in an open-loop or closed-loop manner.

The closed-loop/open-loop control device (9) has a storage device (9a) in which target values or target ranges are stored for the comfort parameters or target values or target ranges are stored for comfort parameter combinations. The closed-loop/open-loop control device (9) compares the data provided by the sensor device (6) with the corresponding target values or target ranges.

Figure 1B:
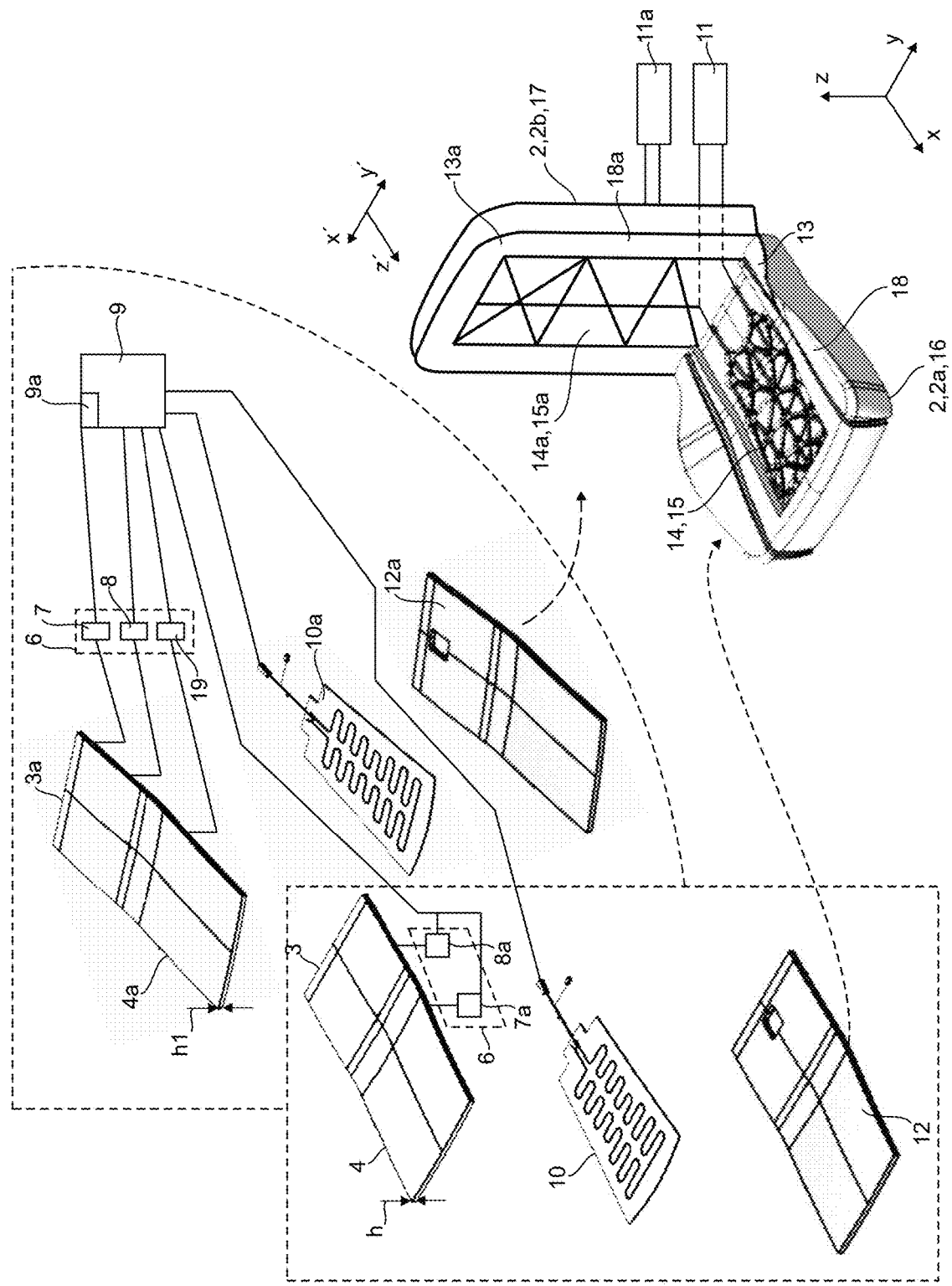
FIG. 1b shows a seat element according to one embodiment of the invention.
Figure 1C:
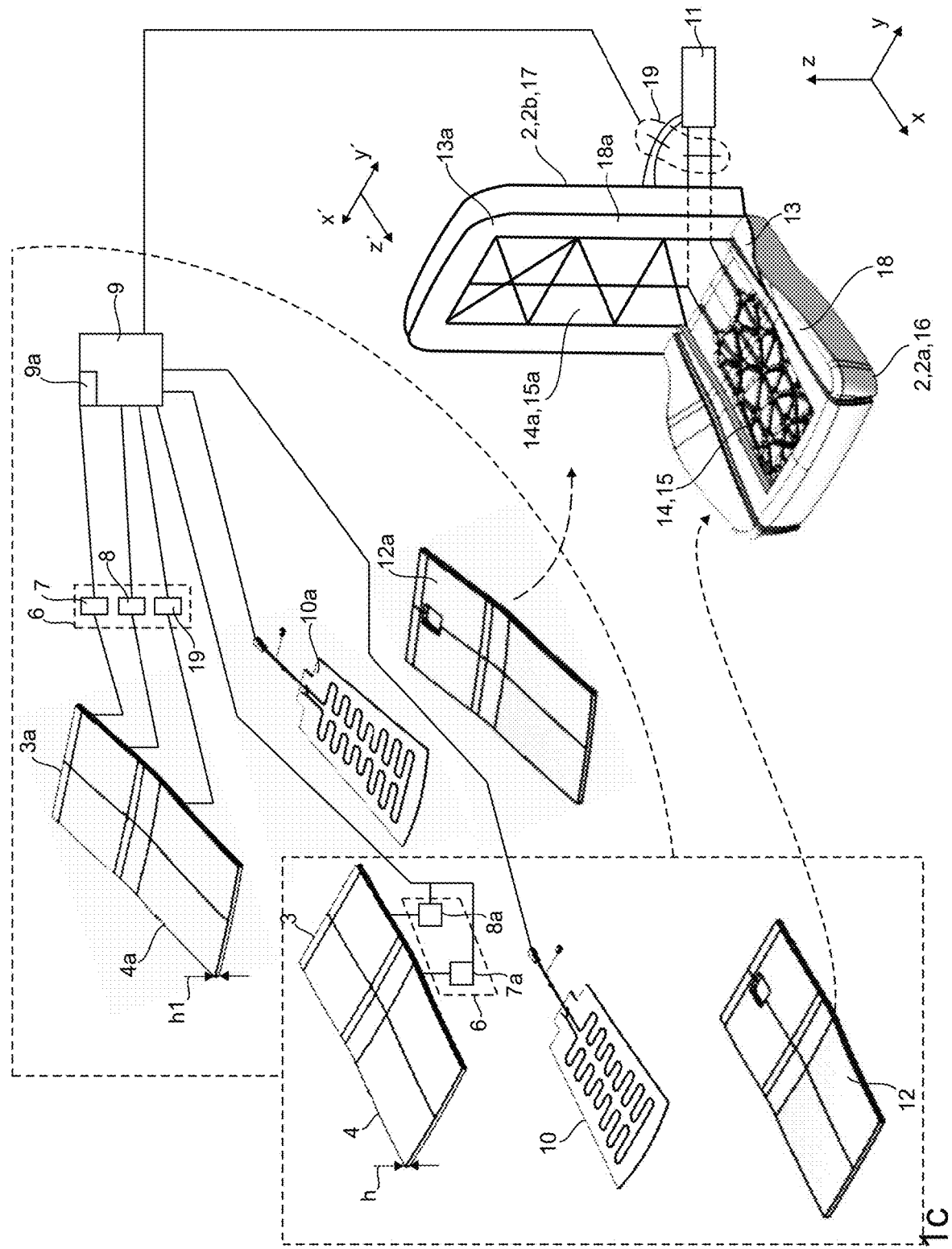
FIG. 1c shows a seat element according to one embodiment of the invention.

The vehicle seat (1) comprises two seat elements (2, 2a, 2b), one seat element (2a) being a lower seat part (16) and the further seat element (2, 2b) being a backrest element (17). This is shown in FIGS. 1b and 1c. In FIG. 1a, only one seat element (2, 2a, 2b) is shown in the form of a lower seat part (16).

The sensor device (6) comprises at least one temperature sensor (7) and at least one moisture sensor (8) for the lower seat part (16) and at least one temperature sensor (7a) and at least one moisture sensor (8a) for the backrest element (17).

The seat elements (2, 2a, 2b) each comprise a height direction Z, Z'. The height direction Z, Z' is to be understood such that the uppermost layer of the seat element (2, 2a, 2b) is that which is in contact with the user and the lowest element is the one which is furthest away from the user. Furthermore, the seat elements (2, 2a, 2b) each comprise a longitudinal direction X, X' and a width direction Y, Y'.

The at least one seat element (2, 2a, 2b) comprises a first layer (3, 3a) which is made of a material that can absorb and conduct moisture, the material of the first layer (3, 3a) being designed so as to be porous and/or open-pored. A surface (4, 4a) of the first layer (3, 3a) is in direct contact with the user or in close proximity to the user when the seat is occupied. It can also be advantageous for this first layer (3) to be covered by a cover, for example a fabric cover.

The sensor device (6) comprises at least one temperature sensor (7) and/or at least one moisture sensor (8), which sensor device is arranged in the at least one seat element (2, 2a, 2b) such that the comfort parameters of temperature and/or moisture can be acquired on or near the surface (4, 4a) of the at least one seat element (2, 2a, 2b). The at least one temperature sensor (7, 7a) and/or the at least one moisture sensor (8, 8a) is/are arranged in and/or above and/or under the first layer (3, 3a), the closed-loop/open-loop control device (9) being evaluated the data transmitted by the sensor device (6) depending on the distance between each sensor (7, 7a, 8, 8a) and the surface (4, 4a) of the at least one seat element (2, 2a, 2b) in contact with the user.

The sensor device (6) is connected to a closed-loop/open-loop control device (9) via signals. The closed-loop/open-loop control device (9) controls the at least one heating device (10, 10a) and/or the at least one ventilation device (11, 11a).

Figure 2:
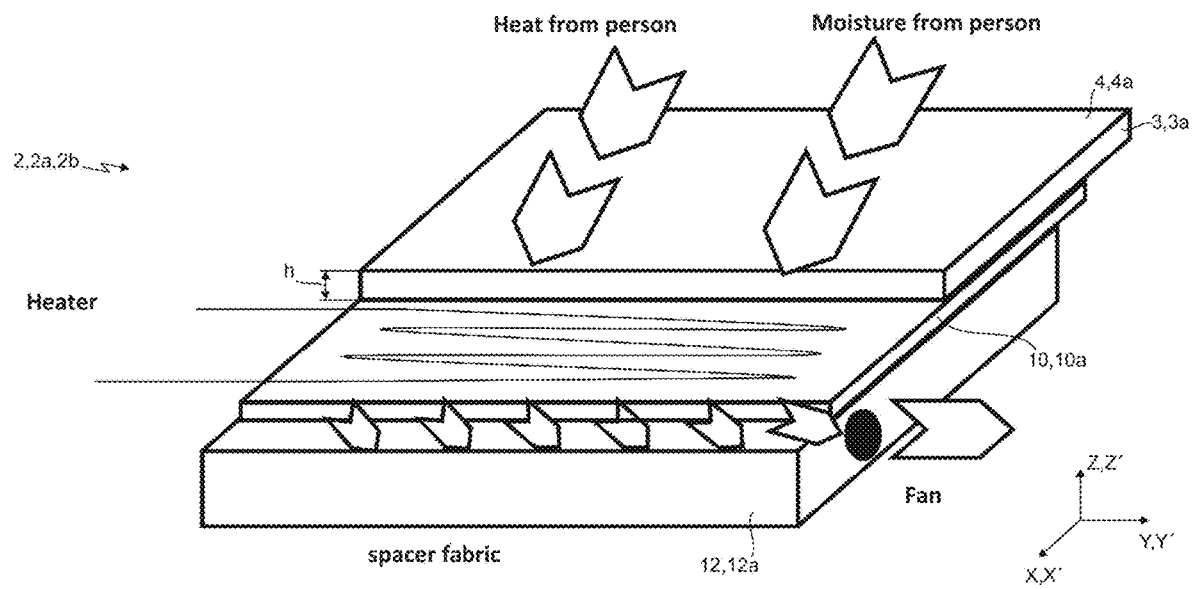
FIG. 2 shows a seat element according to one embodiment of the invention.

In FIGS. 1a, 1b, and 2, it can be seen that at least one heating device (10, 10a) is arranged under the first layer (3, 3a) in the height direction (Z, Z') of the seat element (2, 2a, 2b). The term "under" the first layer (3, 3a) is understood to mean that at least one heating device (10, 10a) can be arranged directly under the first layer (3, 3a) or that further layers with different functionalities and properties can be present between the first layer (3, 3a) and the at least one heating device (10, 10a). The at least one heating device (10, 10a) is advantageously arranged over the surface, preferably over the entire surface, under the first layer (3, 3a).

According to a further embodiment, a (knitted) spacer fabric (12, 12a) is arranged in the height direction (Z, Z') of the seat element (2, 2a, 2b) under the first layer (3, 3a). The term "under" the first layer (3, 3a) is to be understood to mean that the spacer fabric (12, 12a) can be arranged directly under the first layer (3, 3a) or that further layers with different functionalities and properties or the heating device (10, 10a) can be present between the first layer (3, 3a) and the spacer fabric (12, 12a).

Furthermore, in the height direction Z, Z' of the seat element (2, 2a, 2b), a shaped element (13, 13a) is arranged at least partially under the spacer fabric (12, 12a). A shaped element (13, 13a) of this type has a fan region (14, 14a) in which a plurality of ventilation ducts (15, 15a) is provided. The shaped element (13, 13a) has a region (18, 18a) bordering the fan region (14, 14a). This bordering region (18, 18a) can extend along the width direction Y, Y' as well as along the longitudinal direction X, X'. The bordering region (18, 18a) extending along the longitudinal direction X, X' is designed as side bolsters.

The ventilation ducts (15, 15a) are connected to the ventilation device (11, 11a). In the embodiment according to FIG. 1b, a ventilation device (11, 11a) is provided for the lower seat part (16) and for the backrest element (17). In the embodiment according to FIG. 1c, both the lower seat part (16) and the backrest element (17) are connected to only one ventilation device (11). A locking device (19) is advantageously provided in this case, by means of which the respective connecting ducts between the ventilation device 11) and the particular seat element (2, 2a, 2b) can be locked. This locking device (20) can be used to determine which seat element (2, 2a, 2b) is being ventilated. Optionally, both seat elements (2, 2a, 2b) can be ventilated at the same time. The locking device (20) is connected to the closed-loop/open-loop control device (9) via signals and is controlled thereby.

The knitted spacer fabric (12, 12a) and the fan region (14, 14a) are arranged over the surface, preferably over the entire surface, under the heating device (10, 10a) or the first layer (3, 3a).

The seat element (2, 2a, 2b) can also have further layers which are located under, above or between the components mentioned. These layers can have different characteristics and also have different properties. It is also possible that the seat structure described can be assembled differently in terms of position and orientation with the components described.

Two or more heating devices (10, 10a) can also be provided in the seat element (2, 2a, 2b) in order to achieve a greater distance from the surface (4, 4a) and to make better use of the boost function described below.

Finally, the sensor device (6) comprises a seat occupancy sensor (19) which detects the seat occupancy.

Figure 3:
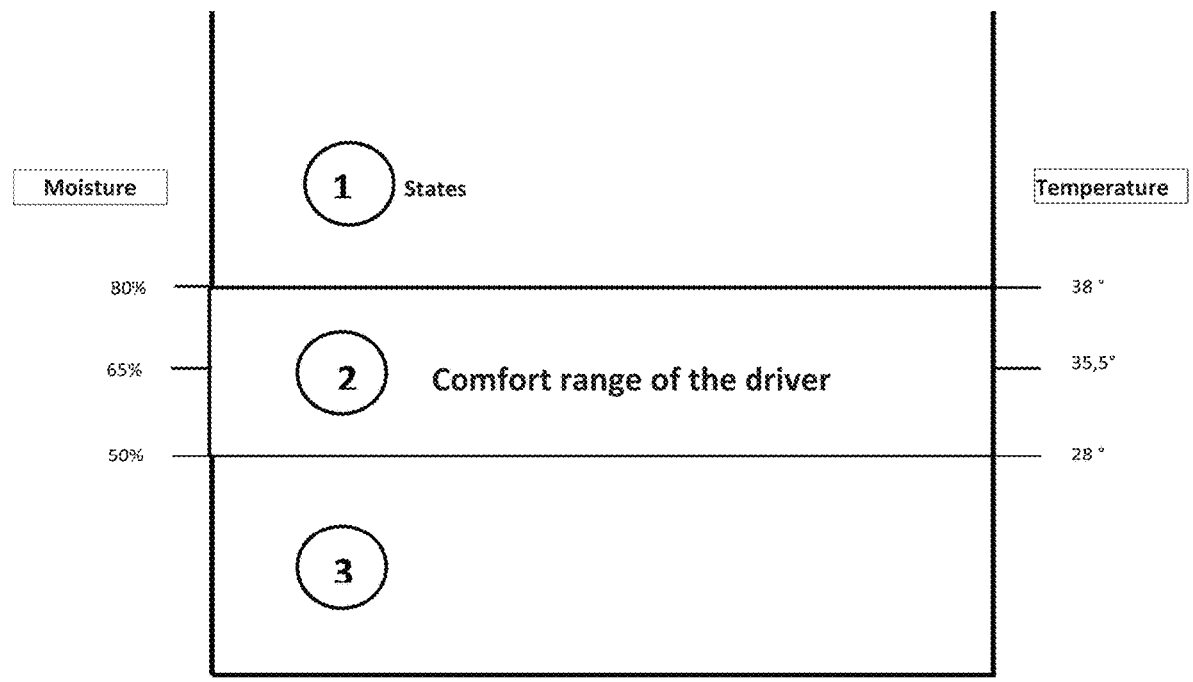
FIG. 3 is a diagram of the user comfort range.

FIG. 3 shows the comfort parameters and a corresponding comfort range of a seat element (2, 2a, 2b). The temperature comfort range is advantageously in a range between 28° C. and 38° C. The moisture comfort range is between 50% and 80% relative moisture. In a defined state 1, the comfort parameters are above the comfort range of the user. If the comfort parameters are in the comfort range, this is state 2. In state 3, the comfort parameters are below a comfort range for the user.

Figure 4:
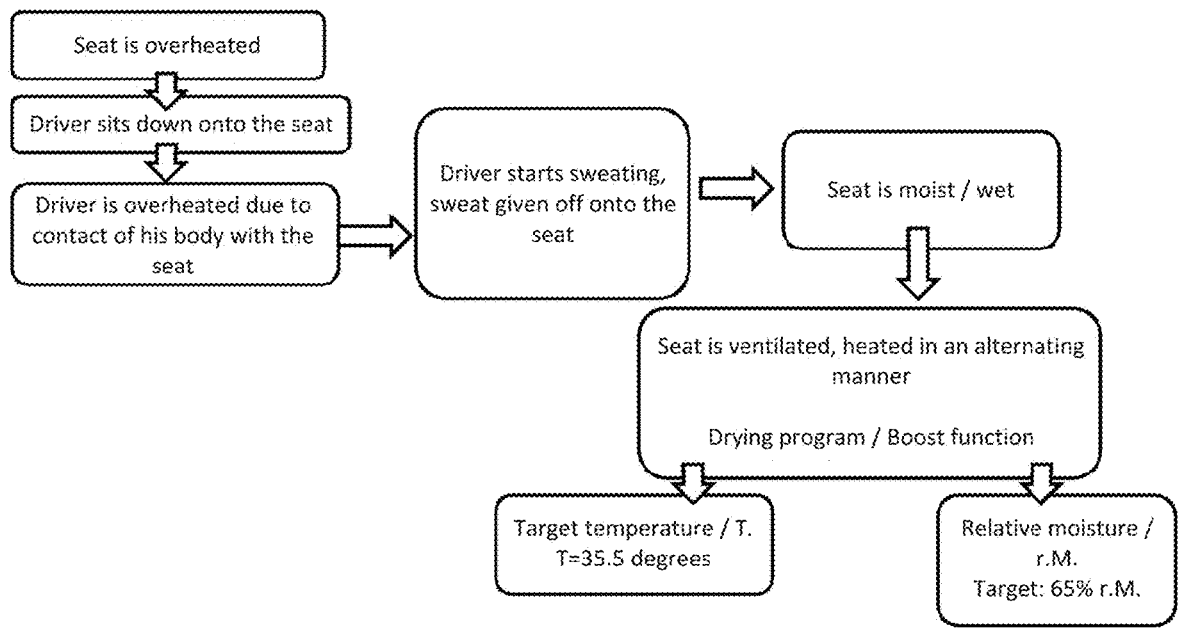
FIG. 4 is a flow chart for seat occupancy.
Figure 5:
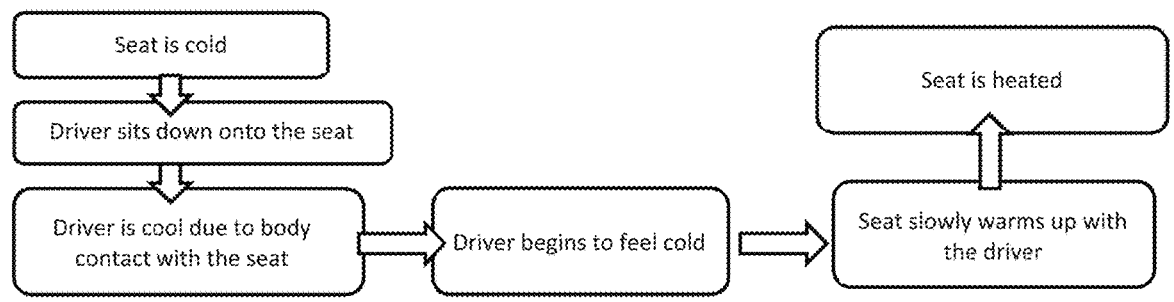
FIG. 5 is a flow chart for seat occupancy.

In FIG. 4, a possible state in winter is shown. The seat is overheated due to the previous manual setting of the seat heating. The user accordingly overheats as a result of body contact with the seat element (2, 2a, 2b). Accordingly, the user sweats. The moisture is absorbed by the first layer (3, 3a) of the seat element (2, 2a, 2b). With the boost function, which is described below, the seat element (2, 2a, 2b) can be dried quickly. An ideal temperature of 35.5° C. and an ideal relative moisture of 65% can thus be set. In the scenario according to FIG. 5, the seat element (2, 2a, 2b) is cold. The driver becomes cool through body contact with the seat element (2, 2a, 2b), as this gives off body heat to the seat (1). The seat element can be heated accordingly by the heating element (10, 10a).

Figure 6:
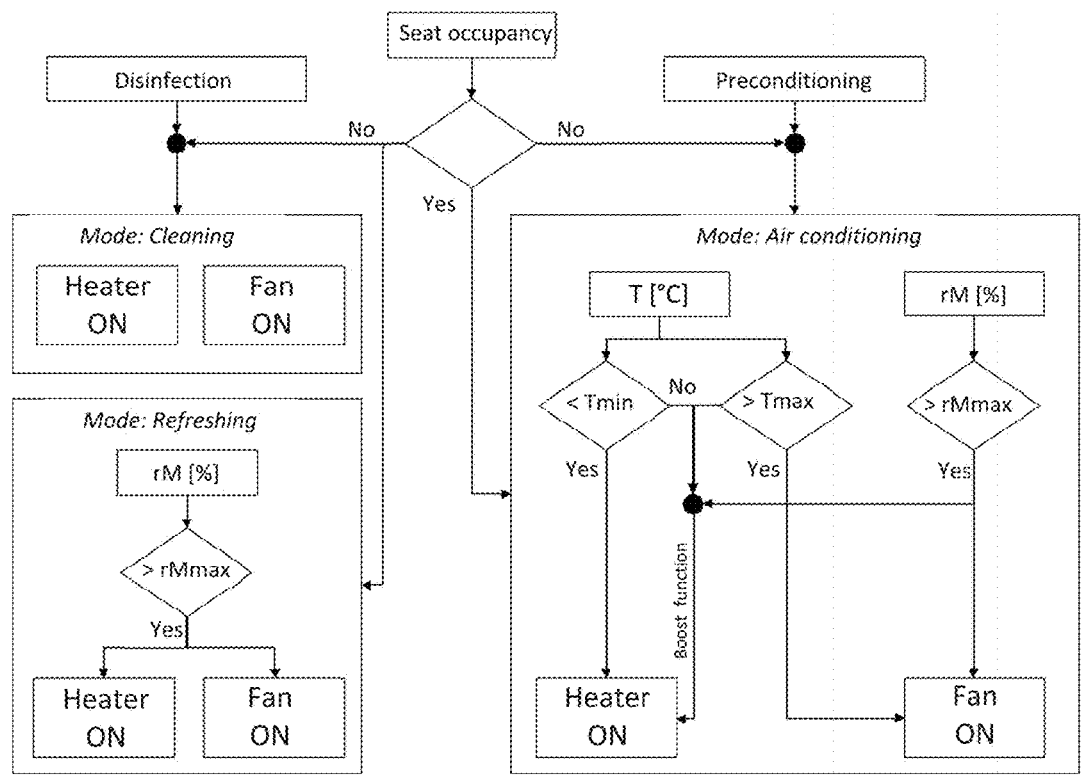
FIG. 6 is a general overview of a flow diagram of a method for operating a seat.
Figure 10:
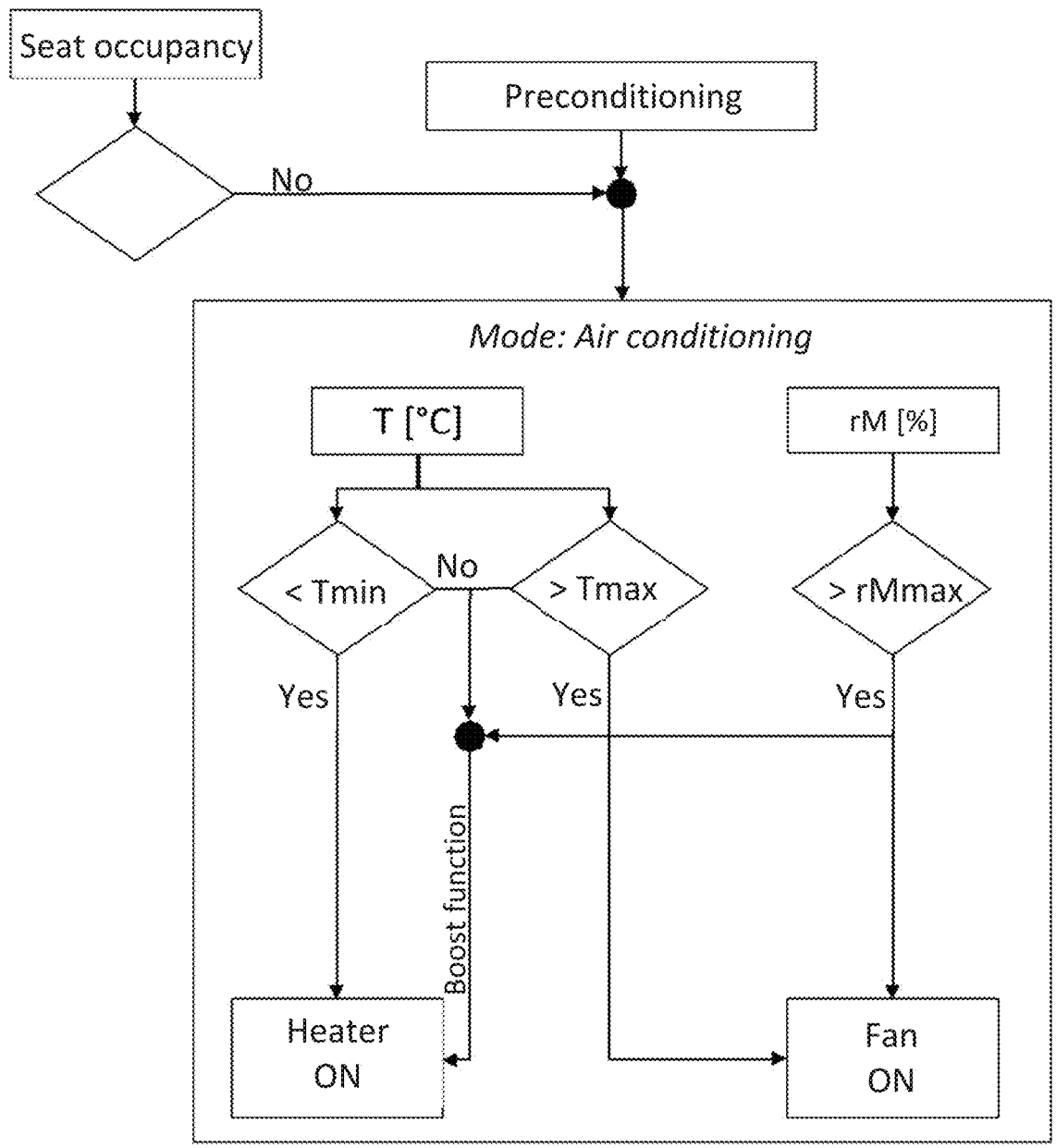
FIG. 10 is a sub-view of a flow diagram of a method for operating a seat.

FIG. 6 shows a general overview of a corresponding flow chart for a method for the preferred operation of a seat (1). FIGS. 7 to 10 show the corresponding sub-overviews. The method preferably offers the following modes: air conditioning with boost function (FIG. 7), refreshing (FIG. 8), cleaning (FIG. 9), disinfecting (FIG. 9) and air conditioning with preconditioning (FIG. 10).

The seat (1) can be cleaned advantageously by activating the heating device (10, 10*a*) and the ventilation device (11, 11*a*). The seat (1) can preferably be cleaned after no seat occupancy has been detected. For this purpose, the first layer (3, 3*a*) is advantageously heated by the heating device (10, 10*a*). As a result of the heating, depending on the temperature, at least some of the moisture contained in the first layer (3, 3*a*) changes into the gaseous state. In addition, the air in the first layer (3, 3*a*) is heated, which can thus absorb more moisture. Steam is thus generated in the first layer (3, 3*a*). Steam of this type can ideally be a pure gaseous phase or a mixture of liquid and gaseous components. By means of the ventilation device (11, 11*a*), the steam is preferably sucked out of the seat element (2, 2*a*, 2*b*) through the knitted spacer fabric (12, 12*a*) and the fan region (14, 14*a*) or the ventilation ducts (15, 15*a*). Alternatively, in the "disinfecting" mode, the first layer (3, 3*a*) can be heated to a temperature above 80° C. This means that existing bacteria can be effectively killed.

In the preferred "refreshing" mode (FIG. 8), the moisture sensor (8) detects a relative moisture in the first layer (3, 3*a*) which is above the comfort range. By advantageously alternating activation of the heating device (10, 10*a*) and the ventilation device (11, 11*a*) by the closed-loop/open-loop control device (9), the relative moisture can quickly be controlled again to a value in the comfort range. The heating in turn produces steam or steam pressure in the seat element (2, 2*a*, 2*b*). By switching on the ventilation device (11, 11*a*) in an alternating manner, this steam can be distributed in the first layer (3, 3*a*) and quickly sucked away. The "refreshing" mode is preferably carried out when the seat is not occupied. The first layer (3, 3*a*) can advantageously be heated to a higher temperature in this case, as a result of which more liquid is correspondingly converted into the gas phase, or the air in the first layer (3, 3*a*) can absorb even more liquid. The seat element (2, 2*a*, 2*b*) can thus be brought back into the comfort range quickly during an occupancy break.

Figure 7:
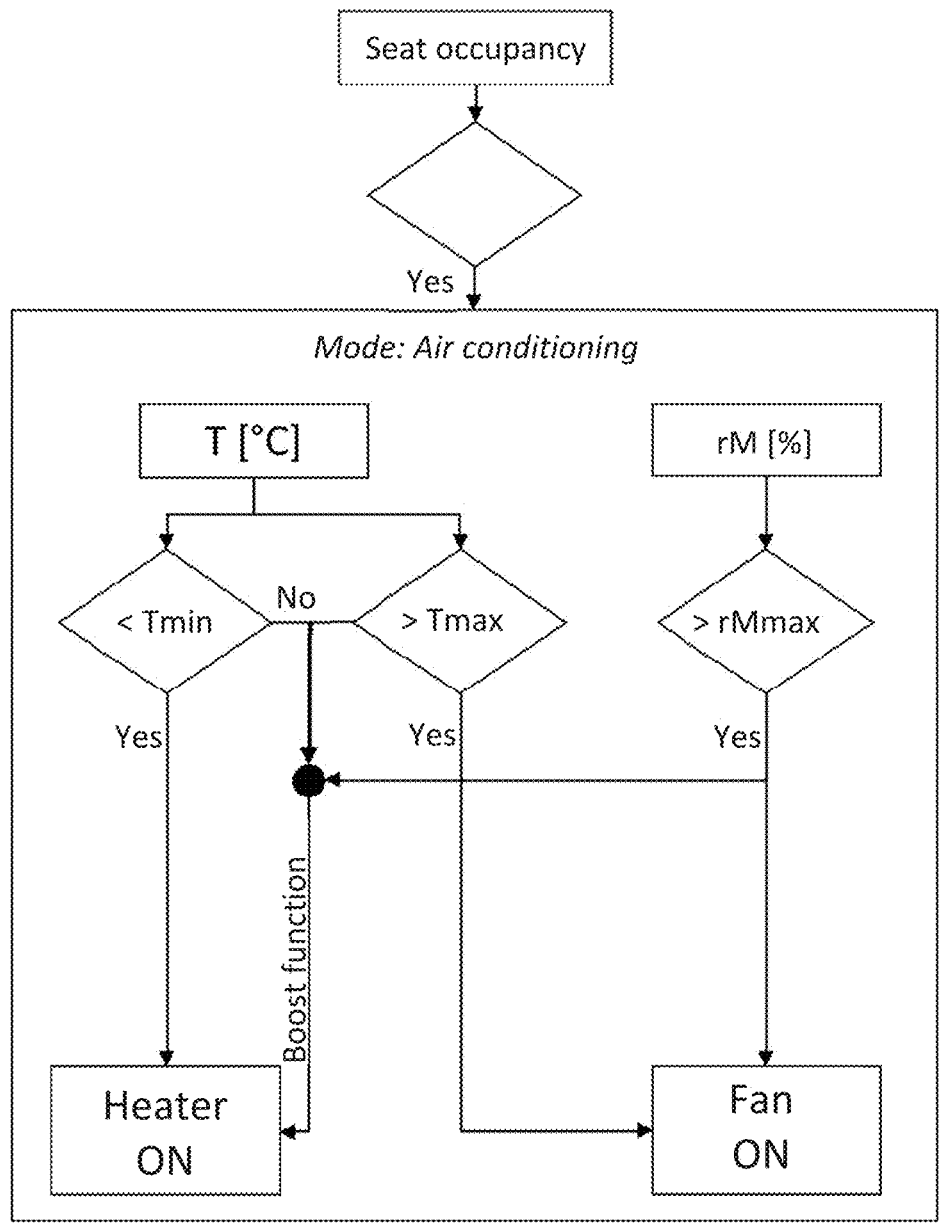
FIG. 7 is a sub-view of a flow diagram of a method for operating a seat.
Figure 8:
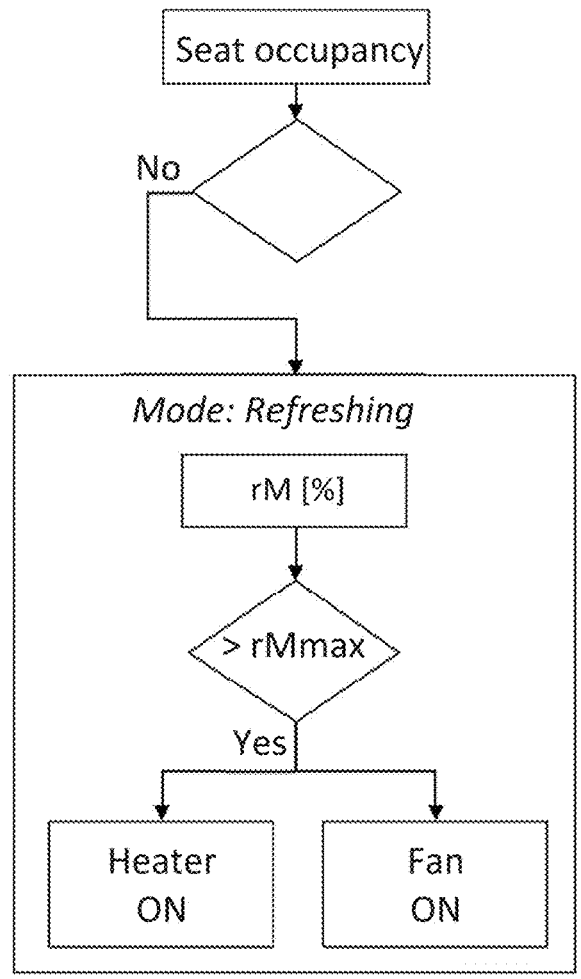
FIG. 8 is a sub-view of a flow diagram of a method for operating a seat.
Figure 9:
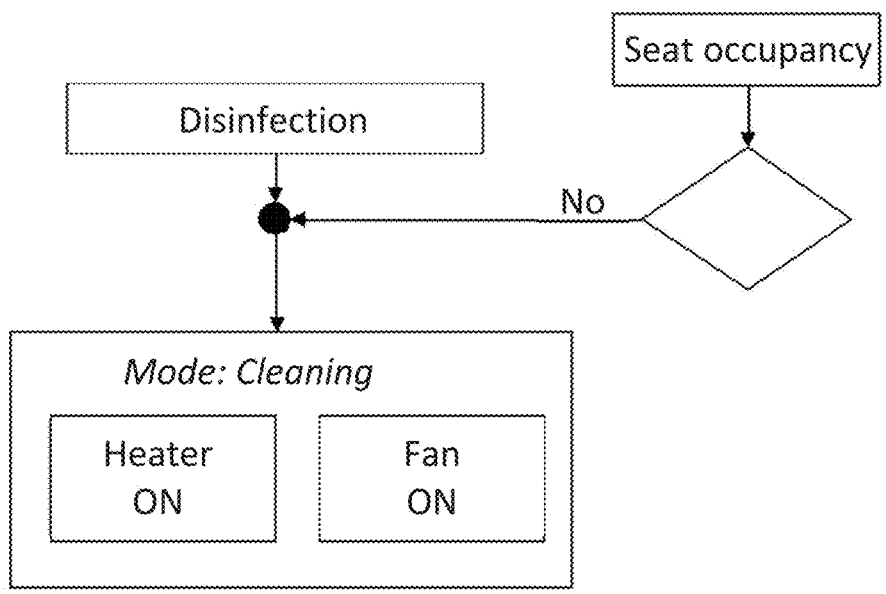
FIG. 9 is a sub-view of a flow diagram of a method for operating a seat.

If seat occupancy is detected, a preferred air conditioning of the seat can take place (FIG. 7). Furthermore, air conditioning of this type can take place after a corresponding advantageous preconditioning, which was carried out before the seat was occupied (FIG. 8). In the "air conditioning" mode, the comfort parameters "temperature" and "relative moisture" are detected by the temperature sensor (7, 7*a*) and the moisture sensor (8, 8*a*).

Figure 11:
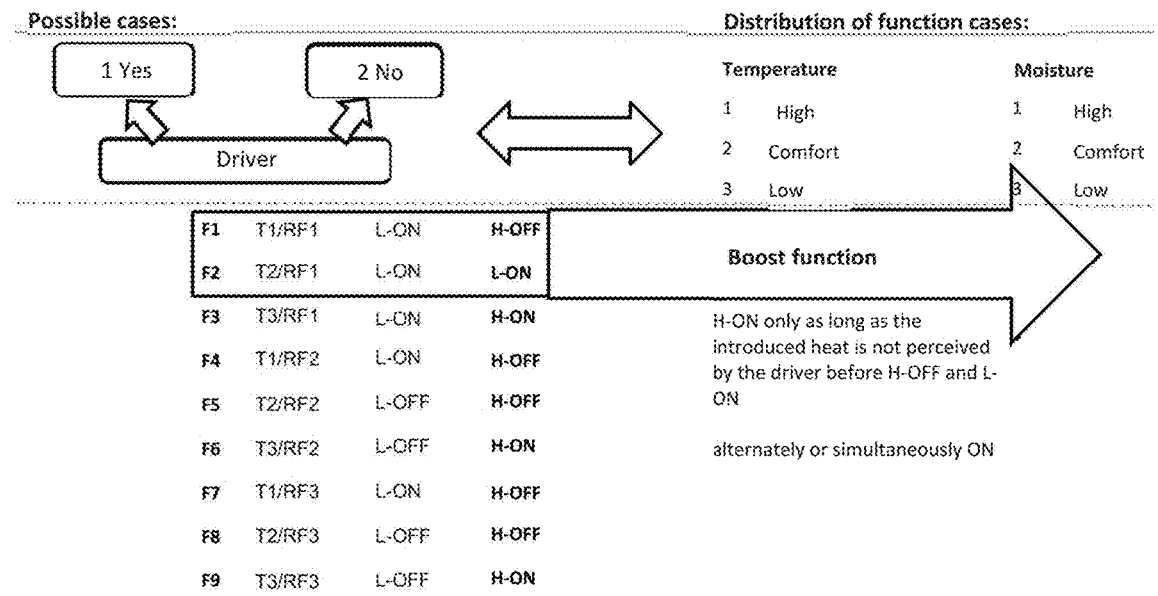
FIG. 11 is a schematic representation of the various cases in a method for operating a seat.

The corresponding preferred scenarios (F1 to F9) are shown in FIG. 11. At a temperature below a minimum temperature (Tmin), the heating device (10, 10*a*) is activated until the predetermined comfort value is reached.

The boost function is preferably activated when the detected relative moisture is above the comfort range or a maximum value (rMmax). At the same time, the temperature is in or above the comfort range, i.e. a maximum temperature (Tmax). These are cases F1 and F2. With this boost function, an additional temperature rise on the surface (4, 4*a*) of the first layer (3, 3*a*) should be prevented from taking place.

For this purpose, the heating device (10, 10*a*) is preferably switched on and off at predetermined intervals. The heating device (10, 10*a*) is advantageously switched on at intervals such that substantially no temperature increase of the surface (4, 4*a*) of the first layer (3, 3*a*) takes place. Usually the heat propagation is inversely proportional to the propagation length of the heat which, in the present case, is at the height (h) of the first layer (3, 3*a*).

Heat conduction is advantageously determined from the thermal coefficient of the first layer (λ), the temperature difference (T) between the heating element, and the surface of the first layer and the height (h) as follows:

$$\lambda * T * 1/h.$$

The interval length is accordingly preferably measured such that the heating device is deactivated before a substantial amount of heat reaches the surface (4, 4*a*) of the first layer (3, 3*a*). An interval length can accordingly be measured such that no substantial temperature change occurs on the surface of the seat element which is perceived by the user. A substantial temperature change is understood to mean a change by 0° C. to 10° C., preferably by 0° C. to 5° C., more preferably by 0° C. to 2.5° C., more preferably by 0° C. to 1° C. Humans detect heat very late, i.e. the surface temperature can be exceeded for a short time without the user noticing.

However, the amount of heat introduced into the first layer (3, 3*a*) is sufficient to generate a sufficient amount of steam, which can then be sucked away by the ventilation device (11, 11*a*). By advantageously repeating the activation of the heating element multiple times, the moisture from the first layer (3, 3*a*) can be heated. Steam can thus be generated which consists of a gas phase and possibly a liquid phase. This steam can then be removed through the ventilation device until the detected moisture value corresponds to a predetermined value in the comfort range. While the heating device (10, 10*a*) is being activated, the ventilation device (11, 11*a*) can be operated continuously. It would also be conceivable for the ventilation device (11, 11*a*) to be activated or deactivated alternately with the heating device (10, 10*a*).

In case F3, the relative moisture is above the comfort range, but the detected temperature value is below the minimum temperature value (Tmin). Accordingly, the boost function is not to be used in this case, since it is intended to supply a specific amount of heat to the surface (4, 4*a*) of the first layer (3, 3*a*).

In case F4, the detected temperature is above the maximum temperature value (Tmax). However, the detected relative moisture is in the comfort range. By activating the ventilation device (11, 11*a*), the temperature can be lowered accordingly. Accordingly, the heating device (10, 10*a*) is not activated.

In case F5, both the detected temperature and the detected relative moisture are in the comfort range. Accordingly, neither the ventilation device (11, 11*a*) nor the heating device (10, 10*a*) are activated.

In case F6, the detected relative moisture is in the comfort range, but the detected temperature is too low. Accordingly, only the heating device (10, 10*a*) is activated.

In case F7, the detected temperature is above the comfort range and the detected relative moisture is below the comfort range. In this case, only the ventilation device (11, 11*a*) is activated for cooling.

In case F8, the detected temperature is in the comfort range and the detected relative moisture is below the comfort range. Neither the heating device (10, 10*a*) nor the ventilation device (11, 11*a*) are activated.

Finally, in case 9, the detected relative moisture and the detected temperature are below the comfort range. Therefore, only the heating device (10, 10*a*) is activated.

Furthermore, a preconditioning of the seat element (2, 2*a*, 2*b*) can preferably take place before the seat is occupied (FIG. 10). In the case of a predeterminable start event, the closed-loop/open-loop control device (9) controls the comfort parameters of the seat element (2, 2*a*, 2*b*) in the comfort range in an open-loop or closed-loop manner. Such a start event can for example be the unlocking of the vehicle, or an approach of the user to the vehicle, which is detected by a corresponding sensor. Alternatively, the comfort parameters can also be set in a comfort range within a predetermined time. For example, the heating device (10, 10*a*) can be activated after the start event in order to bring the surface (4, 4*a*) into the comfort range.

Figure 12:
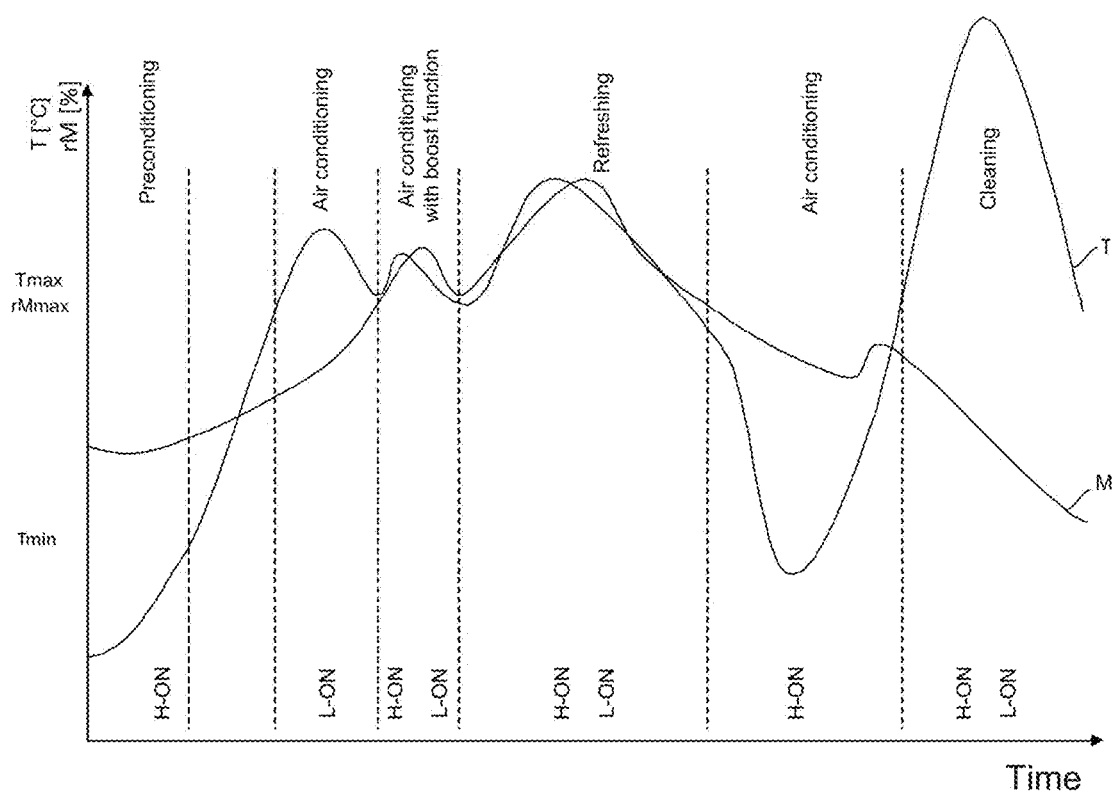
FIG. 12 is a schematic representation of the various cases in a method for operating a seat.

FIG. 12 shows how the comfort parameters change accordingly in the different modes by activating the heating device (10, 10*a*) or the ventilation device (11, 11*a*).

In order to be able to use the boost function better, it can be advantageous if two or more heating devices (10, 10*a*) are provided in the seat element (2, 2*a*, 2*b*).

The "refreshing", "preconditioning" and "disinfecting" modes can also be carried out on seat elements that only have one heating device.

Similarly, preconditioning can also be carried out on a seat element (2, 2*a*, 2*b*) which only has one ventilation device (11, 11*a*, 11*b*). For example, the seat element can be cooled accordingly in summer.

The applicant reserves the right to claim all the features disclosed in the application docu-ments as essential to the invention, provided that these are novel individually or in combination over the prior art.

LIST OF REFERENCE SIGNS

1 Seat
2, 2*a*, 2*b* Seat element
3, 3*a* First layer
4, 4*a* Surface
6 Sensor device
7, 7*a* Temperature sensor
8, 8*a* Moisture sensor
9 Closed-loop/open-loop control device
9*a* Storage device
10, 10*a* Heating device
11, 11*a* Ventilation device
12, 12*a* spacer fabric
13, 13*a* Shaped element
14, 14*a* Fan region
15, 15*a* Ventilation ducts
16 Lower seat part
17 Backrest element
18, 18*a* Bordering region
19 Seat occupancy sensor
20 Locking device
Z Height direction of the lower seat part
Z' Height direction of the backrest element
X Longitudinal direction of the lower seat part
X' Height direction of the backrest element
Y Width direction of the lower seat part
Y' Width direction of the backrest element
h Height of the first layer

The invention claimed is:

1. A vehicle seat comprising at least one seat element in which a heater and a ventilator are provided,
wherein the at least one seat element comprises a lower seat part and a backrest element,
wherein the vehicle seat comprises a sensor that has at least one temperature sensor and at least one moisture sensor, a closed-loop controller controlling at least one of the heater and the ventilator in a closed-loop on a basis of data from the sensor with respect to comfort parameters of at least one of temperature and moisture content, whereby the temperature and the moisture content of the seat can be actively controlled in the closed-loop, the at least one seat element comprising a first layer that is made of a material that can absorb and conduct moisture, the at least one seat element configured to be heated by the heater, whereby moisture absorbed in the first layer changes at least into a gas and air in the at least one seat element when the at least one seat element is heated, wherein the gas generated by the heating is conveyed out of the at least one seat element by the ventilator, the gas being sucked out of the at least one seat element by the ventilator,
wherein a change in a physical state of the moisture results in a cooling of a surface of the at least one seat element due to an evaporative heat applied, a differential pressure prevailing with respect to a surrounding air volume due to an increased temperature of the gas, which pressure facilitates removal of the gas,
wherein the ventilator works in a suction mode, wherein a boost function is activated when a detected relative moisture is above a comfort range or a maximum value and a detected temperature is in or above the comfort range to prevent an additional temperature rise on the surface of the least one seat element, and wherein the heater is switched on and off at predetermined time intervals having a length measured such the heater is deactivated before a substantial amount of heat reaches a surface of the first layer.

2. The vehicle seat according to claim 1, wherein the closed-loop controller has a storage in which at least one of target values and target ranges are stored for the comfort parameters or target values or target ranges are stored for comfort parameter combinations, the closed-loop controller comparing the data provided by the sensor with a corresponding at least one of target values and target ranges.

3. The vehicle seat according to claim 1, wherein the sensor comprises the at least one temperature sensor and the at least one moisture sensor for the lower seat part and the at least one temperature sensor and the at least one moisture sensor for the backrest element.

4. The vehicle seat according to claim 1, wherein the material of the first layer is designed so as to be at least one of porous and open-pored, a surface of the first layer being in direct contact with a user when the vehicle seat is occupied or in close proximity to the user when the vehicle seat is occupied.

5. The vehicle seat according to claim 4, wherein a spacer fabric is arranged under the first layer in a height direction of the at least one seat element, the heater being arranged between the first layer and the spacer fabric.

6. The vehicle seat according to claim 5, wherein a shaped element is arranged at least in portions under the spacer fabric in the height direction of the at least one seat element, wherein the shaped element has a fan region in which a plurality of ventilation ducts is provided, the plurality of ventilation ducts being connected to the ventilator, the shaped element having a region bordering the fan region.

7. The vehicle seat according to claim 1, wherein at least one of the at least one temperature sensor and the at least one moisture sensor are arranged in the at least one seat element such that the comfort parameters of at least one of the temperature and the moisture can be acquired at least one of on and near the surface of the at least one seat element, the at least one of the at least one temperature sensor and the at least one moisture sensor being arranged at least one of in, above, and under the first layer, the closed-loop controller configured to evaluate the data transmitted by the at least one temperature sensor and the at least one moisture sensor depending on a distance between the at least one temperature sensor and the at least one moisture sensor and the surface of the at least one seat element in contact with a user.

8. The vehicle seat according to claim 1, wherein the sensor comprises a seat occupancy sensor which detects a seat occupancy.

9. The vehicle seat according to claim 1, wherein the control of the temperature and the moisture of the seat takes place by alternating heating and ventilating of the first layer, wherein the heater and the ventilator are switched on and off at predetermined intervals, the heater being switchable at intervals such that substantially no temperature change takes place on the surface of the at least one seat element.

10. A method for operating the vehicle seat according to claim 1, the vehicle seat comprising at least one seat element in which at least one heater and at least one ventilator are provided, the method comprising:
   a) Acquiring sensor data by a sensor which has at least one temperature sensor and at least one moisture sensor;
   b) comparing the acquired sensor data with predetermined target values by the closed-loop controller;
   c) activating at least one of at least one the heater and the at least one ventilator by the closed-loop controller, the at least one seat element comprising a first layer which is made of a material that can absorb and conduct moisture, wherein the at least one seat element is heated by the at least one heater, whereby moisture absorbed in the first layer changes at least into a gas and air in the seat element is heated, the gas generated by the heating being able to be conveyed out of the at least one seat element by the at least one ventilator, the gas being sucked out of the at least one seat element by the at least one ventilator, wherein a change in a physical state of the moisture results in a cooling of a surface of the at least one seat element due to an evaporative heat applied, a differential pressure prevailing with respect to a surrounding air volume due to the increased temperature of the gas, which pressure facilitates a removal of the gas, wherein the ventilator works in a suction mode.

11. The method according to claim 10,
wherein when the vehicle seat is not occupied, an antibacterial cleaning of the at least one seat element is carried out by the closed-loop controller in which the at least one heater is activated so that the at least one seat element is brought to a temperature at which bacteria and germs are killed, this temperature being over 80° C.

12. The method according to claim 10,
wherein when the vehicle seat is occupied, the at least one heater and the at least one ventilator are activated at alternating intervals by the closed-loop controller, an interval length for activation of the at least one heater being designed such that there is substantially no temperature change on the surface of the at least one seat element.

13. The method according to claim 10,
wherein when the vehicle seat is not occupied, the at least one heater and the at least one ventilator are activated at alternating intervals by the closed-loop controller, an interval length for activation of the at least one heater being designed such that the at least one seat element is heated to a temperature which is above a predetermined comfort range, the predetermined comfort range of the temperature being between 28° C. and 38° C.

14. The method according to claim 10,
wherein when a predetermined start event occurs, a preconditioning of the at least one seat element takes place, during which comfort parameters are brought into a predetermined comfort range by the closed-loop controller by activating the at least one heater and the at least one ventilator.

15. The vehicle seat according to claim 1, wherein the control of the temperature and the moisture of the seat takes place by alternating heating and ventilating of the first layer, wherein the heater and the ventilator are switched on and off at predetermined intervals, the heater being switchable at intervals such that substantially no temperature change takes place on the surface of the at least one seat element, and wherein while the heater is switched on the ventilator is switched off, and while the heater is switched off the ventilator is switched on.

* * * * *